US007027552B2

(12) United States Patent
Shechter

(10) Patent No.: US 7,027,552 B2
(45) Date of Patent: Apr. 11, 2006

(54) HIGH RESOLUTION CT SCANNER

(75) Inventor: Gilad Shechter, Haifa (IL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 10/513,735

(22) PCT Filed: May 6, 2002

(86) PCT No.: PCT/IL02/00355

§ 371 (c)(1),
(2), (4) Date: Nov. 5, 2004

(87) PCT Pub. No.: WO03/094115

PCT Pub. Date: Nov. 13, 2003

(65) Prior Publication Data

US 2005/0152490 A1    Jul. 14, 2005

(51) Int. Cl.
*A61B 6/03* (2006.01)
(52) U.S. Cl. .................. 378/4; 378/8; 378/901
(58) Field of Classification Search .............. 378/4, 378/8, 15, 19, 901
See application file for complete search history.

(56) References Cited

U.S. PATENT DOCUMENTS

| 5,416,815 A | | 5/1995 | Hsieh |
| 5,475,726 A | * | 12/1995 | Azevedo et al. ............ 378/4 |
| 5,802,134 A | | 9/1998 | Larson et al. |
| 2003/0081821 A1 | * | 5/2003 | Mertelmeier et al. ....... 382/131 |

FOREIGN PATENT DOCUMENTS

FR    2 655 751    6/1991

OTHER PUBLICATIONS

Sahiner, B., et al.; Time-frequency distribution inversion of the Radon transform; IEEE Nuc. Sci. Symposium; 1991; pp. 2043-2047.
Kachelriess, et al.; Advanced Single-Slice Rebinning in Cone-Beam Spiral CT; Medical Physics; 2000; 27;4: 754-772.
Wang, et al.; A General Cone-Beam Reconstruction Algorithm; IEEE Trans. on Medical Imaging; 1993; 12:486-496.

* cited by examiner

*Primary Examiner*—David V Bruce
(74) *Attorney, Agent, or Firm*—Thomas M. Lundin

(57) ABSTRACT

CT scanner is disclosed for providing an image of a region comprising: at least one X-ray cone beam for illuminating mthe region with X-rays; a plurality of rows of X-ray detectors that generate signals responsive to line attenuation of X-rays from the at least one controller that controls providing an image of a region comprising: at least one X-ray cone beam for illuminating the region with X-rays; a plurality of rows of X-ray detectors that generate signals responsive to line attenuation of X-rays from the at least one X-ray source that pass through the region; a controller that controls the at least one X-ray cone beam to acquire line attenuation data for the region for different view angles of the region; and a processor that receives the signals and: a) determines low spatial frequency components of the image from the data; b) generates a first spatial image of the region from the low high spatial frequency components of the image from the data; d) generates a second spatial image of the region from the high frequency components; and e) combines the first and second images to generate the CT image.

47 Claims, 8 Drawing Sheets

HIGH RESOLUTION CT SCANNER

FIELD OF THE INVENTION

The present invention relates to computerized tomography (CT) X-ray imaging and in particular to methods for generating high-resolution CT images.

BACKGROUND OF THE INVENTION

In CT X-ray imaging of a patient, X-rays are used to image internal structure and features of a region of the patients body. The imaging is performed by a CT-imaging system, hereinafter referred to as a "CT scanner", which generally comprises an X-ray source and an array of closely spaced X-ray detectors positioned to face the X-ray source. The X-ray source and array of detectors are mounted in a gantry so that a person being imaged with the CT scanner, generally lying on an appropriate support couch, can be positioned within the gantry between the X-ray source and the array of detectors. The gantry and couch are moveable relative to each other so that the X-ray source and detector array can be positioned axially, along a "z-axis", at desired locations along the patient's body. The gantry comprises a stationary structure, referred to as a stator, and a rotary element, referred to as a rotor. The rotor is mounted to the stator so that the rotor, is rotatable in a plane perpendicular to the z-axis about a center, referred to as an "isocenter", of the rotor. The z-axis is usually chosen for convenience to pass through the rotor isocenter so that the rotor rotates about the z-axis.

In third generation CT scanners the X-ray source and detectors are mounted to the rotor. Some, generally older, "single-slice" third generation CT scanners image a region of a patient by imaging a plurality of relatively thin slices of the region, one slice at a time. A single-slice third generation CT scanner comprises a single, generally curved row of detectors located along an arc of a circle that has its plane perpendicular to the z-axis and its center located at a "focal spot" of the scanner's X-ray source. The X-ray source provides a planar, fan-shaped X-ray beam for illuminating the X-ray detectors with X-rays. The fan beam emanates from the focal spot of the X-ray source and is coplanar with the row of X-ray detectors. A vertex angle of the fan beam is referred to as a "fan angle" and a bisector of the fan angle is referred to as an "axis" of the fan beam.

In fourth generation CT scanners, the X-ray detector array comprises detectors positioned around the perimeter of a circle to form a full circle of detectors. The circle of detectors is stationary and the X-ray source is mounted to the rotor and rotates with the rotor. A single-slice fourth generation CT scanner comprises a single circle of X-ray detectors and a fan beam for illuminating the detectors with X-rays. A fourth generation scanner operates similarly to a third generation scanner and the following discussion which generally refers to third generation configurations of CT scanners relates to fourth generation CT scanners as well, with appropriate adjustments readily understood by persons of the art.

In some single slice CT scanners, to image a region of a patient, the patient is moved stepwise along the z direction to "step" the region through the gantry that houses the X-ray source and detector array. Following each step, the X-ray source is rotated around the isocenter to illuminate a thin slice of the region with X-rays from a plurality of different, usually equally spaced angles, referred to as "view angles". Generally, the X-ray source is rotated through an angle of 360° or (180+Φ) degrees, where Φ is an angular width of the fan angle of the fan beam provided by the X-ray source. A "step and rotate" scan is referred to as an "axial scan".

At each view angle, each detector in the array of detectors measures intensity of X-rays from the source that pass through the slice along an "attenuation path" from the X-ray source to the detector. The measured intensity provides a value for a line integral of the absorption coefficient of the material along the attenuation path. (The line integral is often, conventionally, referred to as a "Radon transform" but will herein be referred to as a line integral. It is further noted that "line integral data" is alternatively referred to herein also as "line attenuation data".) The set of line integral values for a slice generated from intensity measurements provided by all the detectors in the detector array for a given view angle of the X-ray source is referred to as a "view" at the view angle.

The set of all the views of the slice is referred to as a "projection" of the slice. A "span" of view angles in a projection refers to an angular difference between a smallest view angle and a largest view angle of views comprised in a projection. For each view angle in a span of a projection, the projection comprises line integrals for a plurality of parallel attenuation paths, each of which passes through the slice at an angle equal to the view angle but at a different distance from the z-axis. A set of line integrals in a projection of a slice for parallel attenuation paths that pass through the slice at an angle equal to a given view angle is referred to as a "parallel" view of the slice at the view angle. In symbols, if the line integral for an attenuation path that passes through the slice at an angle $\phi$ and a distance s from the z axis is represented by $R(\phi,s)$ and the parallel view at angle $\phi$ having N samples is represented by $PV(\phi,N)$ then $PV(\phi,N)=\{R(\phi, s_1), R(\phi, s_2) \ldots R(\phi, s_N)\}$. To distinguish between a parallel view at a view angle and a view provided by a fan beam at the view angle (for which each attenuation path passes through the slice at different angle) the latter view will hereinafter be referred to as a "fan beam view".

Let a function "$R_\phi(s)$" of s having a value equal to the line integral $R(\phi,s)$ for a given constant angle $\phi$ be referred to as a Radon function at the angle $\phi$. It is noted that the Radon functions at view angle $\phi$ and $(\phi+180°)$ are the same. A convention is therefore used hereinafter that an angle of a Radon function is greater than or equal to 0° and less than 180°. The set of line integrals at different distances s from the isocenter that are comprised in parallel views $PV(\phi,N)$ and $PV(\phi+180°,N)$ at angles $\phi$ and $(\phi+180°)$ respectively provide samples for the same Radon function $R_\phi(s)$.

To generate an image of a slice from a projection of the slice, each parallel view of the slice provided by the projection is used to generate a Fourier transform of a corresponding Radon function of the slice. The Fourier transforms of the Radon functions provide values for a two-dimensional Fourier transform of the X-ray absorption coefficient of tissue in the slice. The two dimensional Fourier transform is processed in accordance with any of various two-dimensional filtered back projection algorithms known in the art to generate a two dimensional spatial function. The spatial function represents the X-ray absorption coefficient of material in voxels of the slice as a function of position of the voxels. The values for the absorption coefficient for the slice are used to characterize and image tissue in the slice. Values of the absorption coefficient for a plurality of contiguous slices in the region of the patient's body can be used to used to provide a three-dimensional image of internal organs in and features of the region.

Resolution of a CT image of a slice generated from attenuation measurements provided by a CT scanner is a function, inter alia, of a sampling rate at which samples, i.e. line integrals, are acquired for each Radon function of the slice. To an extent that the number of samples acquired for a Radon function increases, a Nyquist sampling rate for the function and a maximum frequency for the Fourier transform of the Radon function increases. As the Nyquist sampling rate increases spatial resolution of the absorption coefficient function and corresponding CT image of the slice increases and approaches an upper limit determined by a size of a cross section of attenuation paths through the slice.

For a fan beam of a CT scanner that is rotated (180°+Φ) about an isocenter located on the fan beam axis, a number of different line integrals provided for each Radon function of the slice is generally equal to the number of detectors in the scanner's detector array. Hereinafter, a fan beam rotated about an isocenter located on the fan beam's axis is said to be "center rotated". Increasing the angle through which a center rotated fan beam is rotated from (180°+Φ) to 360° does not increase the number of samples acquired for each Radon function of a slice. For a center rotated fan beam, rotated through 360°, X-ray detectors on opposite sides of the fan beam axis provide line integrals for same attenuation paths through the slice. Parallel views of the slice at view angles $\phi$ and ($\phi$+180°) provide line integrals for the same attenuation paths through the slice and for the same Radon function $R_\phi(s)$.

To double a number of different line integrals acquired for each Radon function of a slice, it is known to offset the fan beam axis from the isocenter and rotate the beam about the isocenter through about 360°. For a fan beam that is "offset rotated" through 360°, X-ray detectors on opposite sides of the fan beam axis provide line integrals for different, generally interleaved, attenuation paths through the slice. In particular a parallel view for a view angle $\phi$ and for a view angle ($\phi$+180°) provide different line integrals for a same Radon function $R_\phi(s)$. A number of samples for the Radon function $R_\phi(s)$ may be doubled by combining the samples provided by the view at view angle $\phi$ and at view angle ($\phi$+180°). Doubling the number of different line integrals acquired for each Radon function of the slice doubles the Nyquist sampling rate for the Radon functions of the slice and generally improves resolution of images generated from attenuation measurements acquired with the fan beam.

In some single slice CT scanners a "helical scan" of a patient is performed instead of an axial scan as described above. In a helical scan, a region of a patient to be imaged is continuously advanced through the gantry while the X-ray source simultaneously continuously rotates around the patient and fan beam views of slices in the region are acquired "on the fly".

The two dimensional filtered back projection algorithms used to generate an image of a slice from "axial scan" line integrals assume that the line integrals of all the fan beam views used to image a slice are for attenuation paths through the patient that are coplanar with the slice. For helical scans, however, no two fan beam views are coplanar. A first fan beam view in a helical scan is displaced along the z-axis from a second fan beam view of the helical scan by a distance determined by the pitch of the helical scan and an angular difference between the view angles of two views. However, usually, for single slice scanners, the pitch of a helical scan is small and for an angular difference of 360° between the view angles of first and second fan beam views, a difference between the z-coordinates of the views is relatively small. As a result, usually, for "helical" single-slice scanners, high resolution, high Nyquist sampling rate data for providing high resolution images can be acquired for each slice using offset rotation of the scanner's fan beam and rotating the beam through 360°.

Modern CT scanners are often multislice scanners designed to simultaneously image a plurality of slices of a patient. A multislice third generation CT scanner comprises a detector array having a plurality of parallel rows of X-ray detectors closely spaced one next to the other along the z-axis direction. The scanner's X-ray source provides a cone shaped beam of X-rays, rather than a planar, fan-shaped X-ray beam for illuminating the X-ray detectors. A multislice fourth generation CT scanner comprises a detector array having a plurality of closely spaced circles of detectors and an X-ray cone beam for illuminating the detectors.

Cone beam geometry may be described with reference to a midplane of the cone beam, which is a plane perpendicular to the z-axis that includes the focal spot of the X-ray source, which generates the cone beam. A vertex angle of the fan-shaped cross section of the cone beam in a plane perpendicular to the midplane that passes through the focal spot is a "cone angle" of the cone beam. For each cone beam view angle a cone beam illuminates a plurality of slices in a region of a patient, where the focal spot of the X-ray source and at least one row of X-ray detectors define each slice. A cone beam view at a given cone beam view angle comprises views acquired with the cone beam for all the slices that the cone beam illuminates at the cone beam angle.

As in the case for single slice scanners, multislice CT scanners can be operated to provide axial scans and/or helical scans of a patient. However, in an axial scan performed by a multislice scanner, the steps are substantially larger than the steps in a single slice scanner. Furthermore, as a cone beam in a multislice scanner is rotated about the z-axis at a fixed z-coordinate, except for views, "midplane views", acquired from X-rays that propagate in the cone beam midplane, none of the views are coplanar. For a helical scan performed by a multislice scanner, the pitch of the helical scan is substantially larger than a pitch of a helical scan performed by a single slice scanner. For a helical scan of a multislice scanner, not only are none of the views acquired by the scanner coplanar, but parallel cone beam views acquired by the scanner for view angles differing by 180° are displaced from each other along the z-axis by relatively large distances. In a helical scan performed by a multislice scanner, the midplane of the scanner's cone beam may be displaced along the z-axis by more than 20 mm in a 360° rotation of the scanners' X-ray source. For both axial and helical scans lack of coplanarity increases as the cone beam angle increases.

As a result, for a multislice scanner having a cone beam characterized by a large cone angle data processing schemes conventionally used for processing data from single slice scanners or from small cone angle multislice scanners may introduce overly obtrusive artifacts in images provided by the scanners. In particular prior art methods for combining parallel views at $\phi$ and ($\phi$+180°) acquired from 360° offset rotation of the scanner's cone beam to generate "high sampling rate" Radon functions and therefrom an image having enhanced resolution may result in and an unacceptable level of artifacts in the image.

U.S. Pat. No. 5,802,134, the disclosure of which is incorporated herein by reference discloses a nutating slice CT image reconstruction apparatus and method for generating a set of projection data that is used to reconstruct a series of planar image slices. A cone beam image reconstruction algorithm is discussed by Ge Wang, et.al. in an article entitled, "A General Cone-Beam Reconstruction Algorithm; IEEE Transactions on Medical Imaging; Vol. 12. No. 3; September 1993. A method of generating images from cone beam data is presented in an article by Marc Kachelriesz et. al. entitled "Advanced single-slice rebinning in cone beam spiral CT"; Med. Phys. 27 (4); April 2000.

SUMMARY OF THE INVENTION

An aspect of some embodiments of the present invention relates to providing methods for improving the resolution of images provided by multislice scanners.

An aspect of some embodiments of the present invention relates to providing a method for processing data for imaging a region of a patient that is previously acquired by a multislice CT scanner in which the scanner's cone beam is offset rotated.

The inventor has determined that in an image of a region generated by a multislice scanner from offset rotation parallel views at $\phi$ and ($\phi+180°$) that are combined to provide high sampling rate Radon functions, artifacts are often caused by low spatial frequency components of the Fourier transform of the region's absorption coefficient generated from the Radon functions. Therefore, in accordance with an embodiment of the present invention, for an image of a region provided by a multislice scanner, low spatial frequency Fourier components of the absorption coefficient for voxels in the region are generated from cone beam views that are not combined to provide high resolution Radon functions. High spatial frequency components of the Fourier transform of the absorption coefficient for voxels are generated from data acquired from offset rotated cone beam views in a view angle span of about 360° that are combined to provide high sampling rate Radon functions.

The low spatial frequency Fourier components of the absorption coefficients are filtered and back projected to determine a "low frequency" absorption coefficient for voxels in the slice and therefrom a "low frequency" image of the voxels. The high spatial frequency components of the absorption coefficients are filtered and back projected to determine a "high frequency" absorption coefficient for voxels in the slice and therefrom a "high frequency" image of the voxels. The low and high frequency images are added to provide a final image of the region.

By generating low frequency components of the Fourier transform of the absorption coefficient from cone beam views that are not combined to provide high resolution Radon functions, artifacts in the image are moderated. The high frequency components of the Fourier transform, which are provided from parallel views at $\phi$ and ($\phi+180°$) that are combined to provide high sampling rate Radon functions, provide for improved resolution of the final image.

In accordance with an embodiment of the present invention, before adding the high frequency image to the low frequency image to produce the final image, the high frequency image is weighted to provide a desired ratio between the low and high frequency images in the final image. Weighting of the high frequency image enables the final image to be smoothed or sharpened as required to provide desired viewing of the imaged region.

There is therefore provided, in accordance with an embodiment of the present invention, a CT scanner for providing an image of a region comprising: at least one X-ray cone beam for illuminating the region with X-rays; a plurality of rows of X-ray detectors that generate signals responsive to line attenuation of X-rays from the at least one X-ray source that pass through the region; a controller that controls the at least one X-ray cone beam to acquire line attenuation data for the region for different view angles of the region; and a processor that receives the signals and:

a) determines low spatial frequency components of the image from the data;

b) generates a first spatial image of the region from the low frequency components;

c) determines high spatial frequency components of the image from the data;

d) generates a second spatial image of the region from the high frequency components; and e) combines the first and second images to generate the CT image.

Optionally, the at least one X-ray cone beam is offset rotated. Additionally or alternatively the at least one X-ray cone beam comprises a plurality of X-ray cone beams.

In some embodiments of the present invention, the controller controls the at least one cone beam to acquire line attenuation data of the region for a span of view angles of about 360°. Optionally, the processor processes the line attenuation data to generate parallel views for the span of view angles.

Optionally, the low frequency spatial components are band limited by a Nyquist frequency $\omega_N$ determined by a number of line integrals in a parallel view. Optionally, the low frequency spatial components are Fourier components.

In some embodiments of the present invention, the high frequency spatial components are band limited by a Nyquist frequency $2\omega_N$ determined by twice a number of line integrals in a parallel view. Optionally, the processor interleaves parallel views having an angular separation of 180° and Fourier transforms the interleaved parallel views to determine the high frequency Fourier components. Optionally, the processor interleaves parallel views with a number of null values equal to a number of line integrals in a parallel view and Fourier transforms the interleaved parallel views to determine the high frequency Fourier components.

Optionally, to generate the second image the processor generates a first partial high frequency image from interleaved parallel views in a portion of the view angle span from 0° to about 180° and a second partial high frequency image from a portion of the view angle span from about 180° to about 360° and combines the first and second partial images.

In some embodiments of the present invention, the processor filters the high frequency data with a high band pass filter $f_H(\omega)$. Optionally, the high frequency filter $f_H(\omega)$ is equal substantially to zero for values of $\omega$ substantially less than $\omega_N$ and values of $\omega$ greater than $2\omega_N$. Additionally or alternatively, $f_H(\omega)$ is substantially equal to one for values of $\omega$ in a neighborhood of $\omega_N$. In some embodiments of the present invention, $f_H(\omega)$ decreases adiabatically to zero at a value $\omega$ in a neighborhood of $2\omega_N$.

In some embodiments of the present invention, the processor filters the low frequency components with a low frequency band pass filter $f_L(\omega)$.

In some embodiments of the present invention, the functions $f_H(\omega)$ and $f_L(\omega)$ are related by an expression $f(\omega)=f_H(\omega)+f_L(\omega)$ where $f(\omega)$ is equal substantially to one for values of $\omega$ substantially less than $\omega_N$ and equal to substantially zero for $\omega$ greater than $2\omega_N$. Optionally, $f(\omega)$ is equal substantially to one for values of $\omega$ in a neighborhood of $\omega_N$. Additionally or alternatively, $f(\omega)$ optionally decreases adiabatically to zero at a value of $\omega$ less than and in a neighborhood of $2\omega_N$.

In some embodiments of the present invention, low frequency filter $f_L(\omega)$ has non-zero values for $\omega$ less than $\omega_N$ and is equal to substantially zero for values of $\omega$ greater than $\omega_N$. In some embodiments of the present invention, $f_L(\omega)$ is equal to substantially one for values of $\omega$ substantially less than $\omega_N$. In some embodiments of the present invention, $f_L(\omega)$ adiabatically, decreases to zero at a value for $\omega$ in a neighborhood of $\omega_N$.

There is further provided, in accordance with an embodiment of the present invention, a method of generating a CT image from line attenuation data of a region comprising: determining low spatial frequency components of the image from the data; generating a first spatial image of the region from the low frequency components; determining high spatial frequency components of the image from the data; generating a second spatial image of the region from the high frequency components; and combining the first and second images to generate the CT image.

Optionally, the line attenuation data comprises data acquired using an offset rotated X-ray cone beam. Optionally, the line attenuation data comprises data acquired using X-ray cone beams provided by a plurality of X-ray sources.

In some embodiments of the present invention, the line attenuation data comprises data from cone beam views of the region in a span of view angles of about 360°.

Optionally, processing the line attenuation data comprises generating parallel views for the span of view angles.

Optionally, determining low frequency spatial components comprises determining frequency components that are band limited by a Nyquist frequency $\omega_N$ determined by a number of line integrals in a parallel view.

Optionally, determining the low frequency spatial components comprises Fourier transforming each parallel view to determine low frequency Fourier components.

Additionally or alternatively, determining high frequency spatial components comprises determining frequency components that are band limited by a Nyquist frequency $2\omega_N$ determined by twice a number of line integrals in a parallel view.

Optionally, determining the high frequency Fourier components comprises generating interleaved parallel views by interleaving data from parallel views having an angular separation of 180° and Fourier transforming the interleaved parallel views to determine high frequency Fourier components.

Optionally, determining the high frequency Fourier components comprises generating interleaved parallel views by interleaving data from each parallel view with a number of null values equal to a number of line integrals in a parallel view and Fourier transforming the interleaved parallel views. Optionally, determining the second image comprises generating a first partial high frequency image from interleaved parallel views in a portion of the view angle span from 0° to about 180° and a second partial high frequency image from a portion of the view angle span from about 180° to about 360° and combining the first and second partial images.

In some embodiments of the present invention, the method comprises filtering the high frequency data with a high band pass filter $f_H(\omega)$. Optionally, high frequency filter $f_H(\omega)$ is equal substantially to zero for values of $\omega$ substantially less than $\omega_N$ and values of $\omega$ greater than $2\omega_N$. Alternatively or additionally $f_H(\omega)$ is substantially equal to one for values of $\omega$ in a neighborhood of $\omega_N$. In some embodiments of the present invention, $f_H(\omega)$ decreases adiabatically to zero at a value $\omega$ in a neighborhood of $2\omega_N$.

In some embodiments of the present invention, the method comprises filtering the low frequency components with a low frequency band pass filter $f_L(\omega)$.

In some embodiments of the present invention, the functions $f_H(\omega)$ and $f_L(\omega)$ are related by an expression $f(\omega)=f_H(\omega)+f_L(\omega)$ where $f(\omega)$ is equal substantially to one for values of $\omega$ substantially less than $\omega_N$ and equal to substantially zero for $\omega$ greater than $2\omega_N$. Optionally, $f(\omega)$ is equal substantially to one for values of $\omega$ in a neighborhood of $\omega_N$. Additionally or alternatively, $f(\omega)$ optionally decreases adiabatically to zero at a value of $\omega$ less than and in a neighborhood of $2\omega_N$.

In some embodiments of the present invention, low frequency filter $f_L(\omega)$ has non-zero values for $\omega$ less than $\omega_N$ and is equal to substantially zero for values of $\omega$ greater than CON. In some embodiments of the present invention, $f_L(\omega)$ is equal to substantially one for values of $\omega$ substantially less than $\omega_N$. In some embodiments of the present invention, $f_L(\omega)$ adiabatically, decreases to zero at a value for $\omega$ in a neighborhood of $\omega_N$.

There is further provided, in accordance with an embodiment of the present invention, a method of generating a CT image of a region from cone beam data comprising: acquiring line attenuation data for first and second parallel views of the region at view angles separated by an angular difference of 180°; interleaving data from each parallel view with null values; generating in accordance with a 3D back projection algorithm first and second images of the region using data in the first and second interleaved views respectively; and combining the first and second images to generate the CT image of the region.

BRIEF DESCRIPTION OF FIGURES

Non-limiting examples of embodiments of the present invention are described below with reference to figures attached hereto and listed below. In the figures, identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION OF EXEMPLARY EMBODIMENTS

Figure 1:
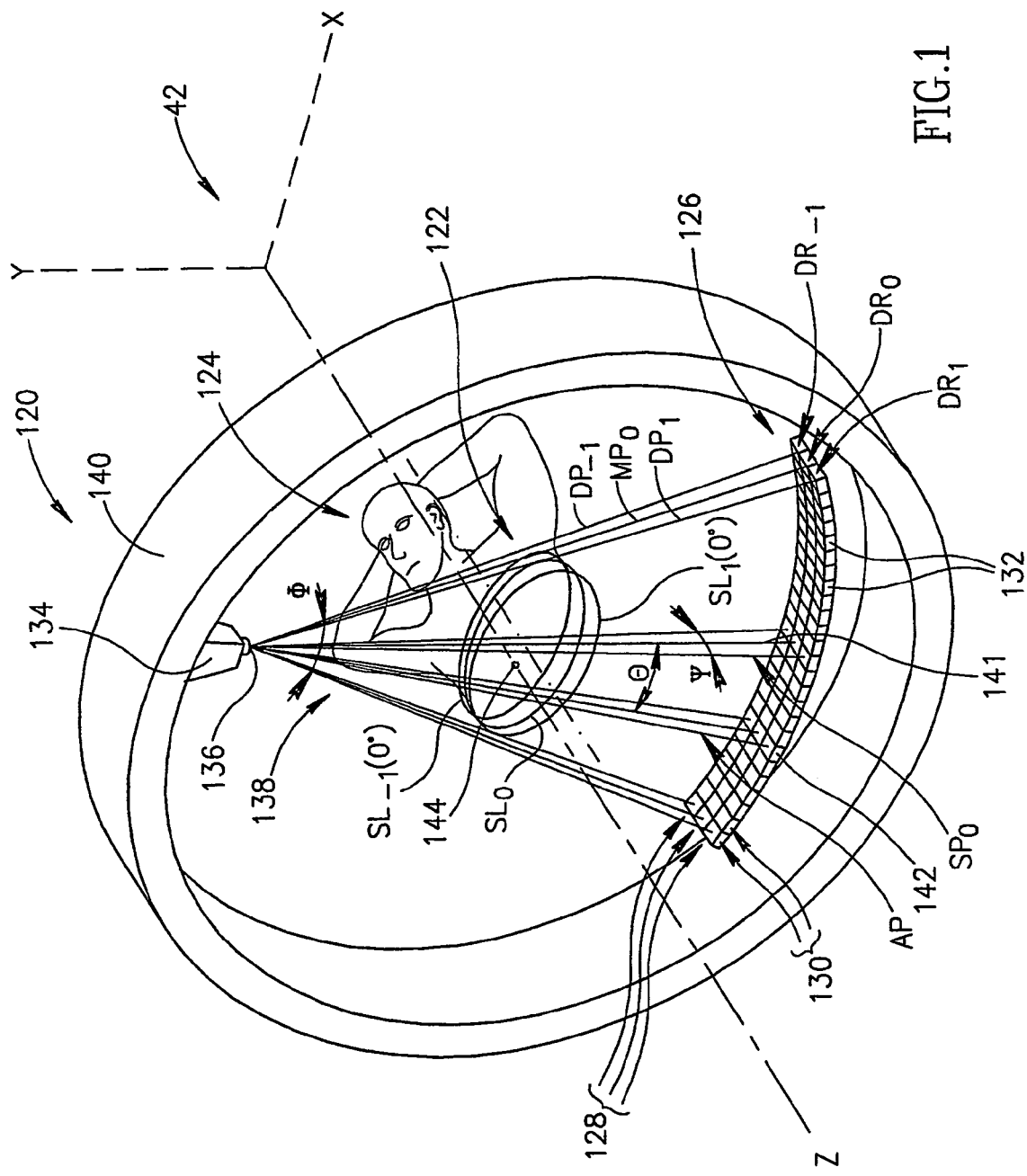
FIG. 1 schematically shows a third generation multislice scanner imaging a region of a patient using a cone beam generated by the scanner, FIG. 2 schematically shows attenuation paths for a cone beam view acquired with the cone beam shown in FIG. 1.

FIG. 1 schematically shows a third generation multislice CT scanner 120 imaging a region 122 of a patient 124. Only features of multislice scanner 120 germane to the discussion are shown in FIG. 1 and only a portion of patient 124 is shown so that features germane to the discussion are clearly visible.

Multislice scanner 120 comprises a detector array 126 having rows 128 and columns 130 of X-ray detectors 132 and an X-ray source 134 having a focal spot 136 that provides a cone beam 138 of X-rays for illuminating region 122 of patient 124. X-ray source 134 and detector array are mounted to a rotor 140 of a gantry (not shown) comprised in multislice scanner 120. Rotor 140 is rotatable around the z-axis of a coordinate system 42. By way of example, detector array 126 is shown comprising three rows 128 of detectors 132, which rows are individualized by labels $DR_0$, $DR_1$ and $DR_{-1}$. Patient 124 is supported on a couch (not shown) during imaging of the patient. The couch is controllable to be translated axially along the z-axis to position region 122 as required between X-ray source and detector array 126.

Cone beam 138 has a midplane $MP_0$ defined by focal spot 136 and detector row $DR_0$, and two "declination planes", $DP_{-1}$ and $DP_1$ defined by focal spot 136 and by detector rows $DR_{-1}$ and $DR_1$ respectively. A vertex angle $\Phi$ of midplane $MP_0$ is a fan angle of cone beam 138 and a bisector 141 of fan angle $\Phi$ is an axis of cone beam 138. A sagittal plane $SP_0$ of cone beam 138 is a plane that passes through axis 141 and is perpendicular to midplane $MP_0$. A vertex angle $\Psi$ of sagittal plane $SP_0$ is a cone beam angle of cone beam 138. A column 130 of detectors 132 and focal spot 136 define a plane parallel to the z-axis, hereinafter referred to as an axial plane, of cone beam 138. An axial plane "AP" of cone beam 138 defined by a given column 130 of detectors 132 makes an angle with sagittal plane $SP_0$ that is referred to as an "azimuthal angle". An axial plane AP for a particular column 142 of detectors 132 is shown in FIG. 1 and its azimuthal angle is indicated as angle $\theta$.

An intersection point 144 of the z-axis with midplane $MP_0$ of cone beam 138 is an isocenter of the scanner. Optionally, as shown in FIG. 1, axis 141 of cone beam 138 is offset from isocenter 144 and cone beam 138 is offset rotated to acquire attenuation measurements and therefrom line integrals for region 122. In FIG. 1 scanner 120 is shown by way of example acquiring attenuation measurements for region 122 at a view angle of 0°.

Multislice scanner 120 can generally be operated in an axial mode or in a helical mode to image region 122 of patient 124. In an axial mode region 122 is stepped axially along the z-axis through rotor 140 of the scanner. Following each step, rotor 140 rotates around the z-axis to rotate X-ray source 134 and cone beam 138 around region 122, generally through 360°, to acquire attenuation measurements along each attenuation path through the region from focal spot 136 to a detector 132 for each of a plurality of cone beam view angles. In a helical mode, region 122 is moved continuously along the z-axis through rotor 140 as rotor 140 simultaneously, continuously rotates around the z-axis to acquire attenuation measurements.

At any view angle $\phi$ of cone beam 138, the cone beam simultaneously illuminates three slices of region 122, a slice in each of midplane $MP_0$, declination plane $DP_{-1}$ and declination plane $DP_1$ and acquires a view for each of the slices. The slices in planes $MP_0$, $DP_{-1}$ and $DP_1$ are schematically shown for $\Phi=0°$ in FIG. 1 by ellipses labeled respectively $SL_0$, $SL_{-1}(0°)$ and $SL_1(0°)$. The labels for "off-midplane" slices $SL_{-1}(0°)$ and $SL_1(0°)$ include as arguments the view angle of cone beam 138 because slices of region 122 that lie in declination planes $DP_1$ and $DP_{-1}$ are different for different view angles $\phi$ of cone beam 138.

In an axial mode scan for a fixed z-axis position of the patient, none of the views of slices of region 122 acquired during rotation of cone beam 138 around the region, except for midplane views, are coplanar. In a helical mode scan none of the views of slices of region 22 acquired by scanner 120 are coplanar. As a result, generally, conventional 2D filtered back projection procedures used to generate an image of a region from data acquired by single slice scanners are not used to generate an image provided by a multislice scanner such as multislice scanner 120, particularly if the multislice scanner has a large cone angle.

In some procedures, cone beam data acquired by each row 128 of detectors 132 during a scan of region 22 is binned to provide parallel views of the region for a plurality of different view angles. Data in the parallel views is interpolated, filtered, weighted and back-projected in accordance with various known 2D or 3D back-projection algorithms to determine absorption coefficients for voxels in region 122 and therefrom an image of the region.

Let a cone beam parallel view at a given view angle for cone beam 138 comprise line integrals for all attenuation paths through region 122 whose projections onto the midplane $MP_0$ make an angle with the y-axis equal to the view angle. Hereinafter for ease of visualization and presentation, projections onto midplane $MP_0$ will be shown and also referred to as projections onto the x-y plane of coordinate system 42. Since attenuation paths that lie in a same axial plane have a same projection on the xy-plane, a cone beam parallel view comprises line integrals for groups of attenuation paths lying in, "belonging to", same axial planes. For exemplary multislice scanner 120 comprising three rows 128 of detectors 132, a cone beam parallel view comprises line integrals for each of a plurality of groups of three attenuation paths. A set of line integrals in a cone beam parallel view for attenuation paths defined by detectors 132 in a same row 128 of detectors 132 is referred to as a parallel view of the cone beam parallel view. Each cone beam parallel view therefore comprises three parallel views, one parallel view for each detector row $DR_0$, $DR_1$ and $DR_{-1}$.

Figure 2:
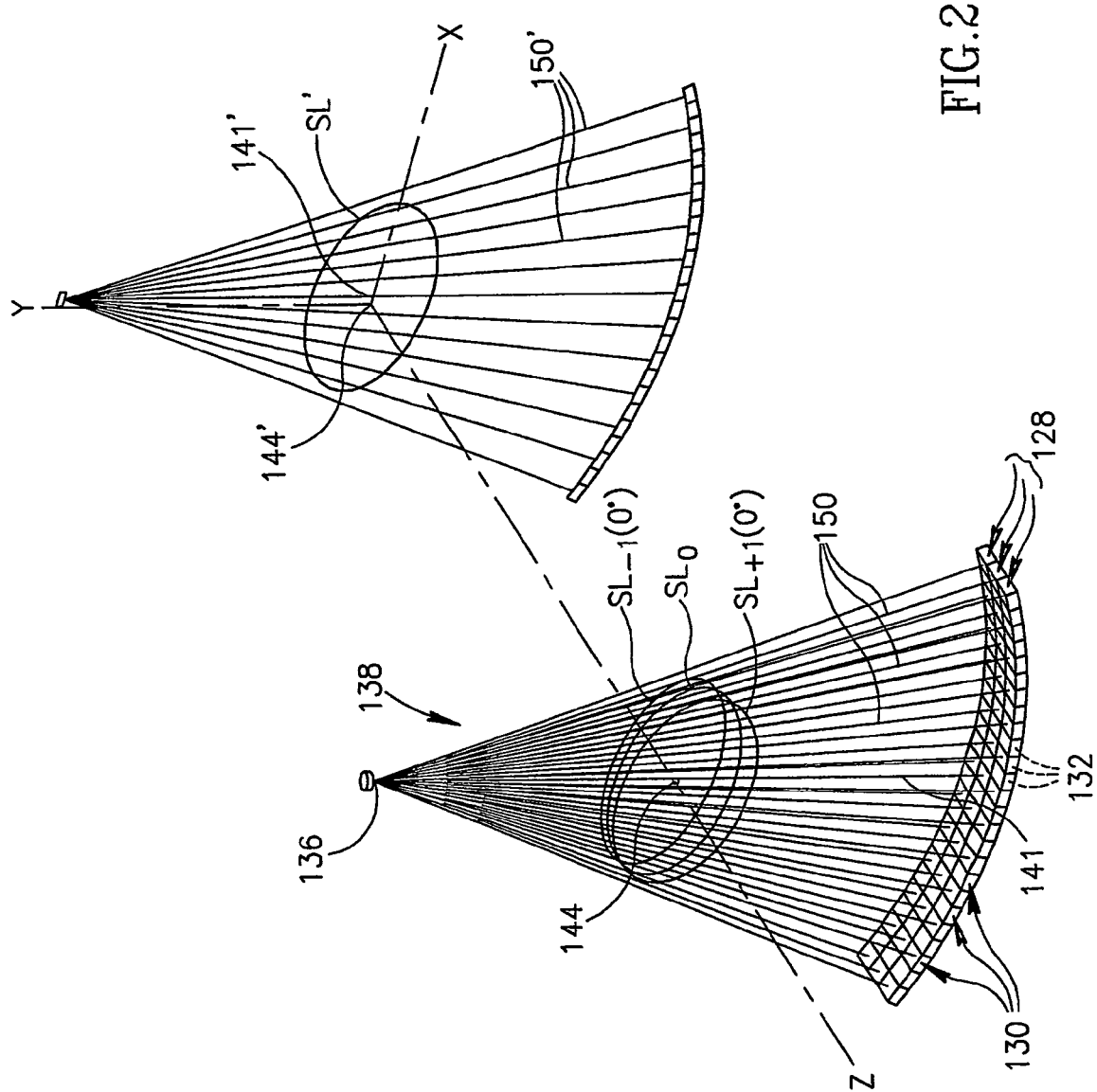

FIG. 2 schematically shows attenuation paths 150 for a cone beam view of region 122 at a view angle of 0° (axis 141 is parallel to the y-axis of coordinate system 42) for cone beam 138. For clarity of presentation attenuation paths 150 are shown for only 13 columns 130 of detectors 132, which columns define 13 axial planes AP (FIG. 1) of cone beam 138. The axial planes AP in FIG. 2 are optionally oriented at equally spaced azimuthal angles. FIG. 2 also shows projections 150' of attenuation paths 150 and a projection SL' of ellipses $SL_0$, $SL_{-1}(0°)$ and $SL_1(0°)$ on the xy-plane. Note that because cone beam 138 is assumed to be offset rotated, a projection 141' of axis 141 of cone beam 138 is offset from the origin of coordinate system 42 and the axis is not coincident with the y-axis. A projection of isocenter 144 on the x-y plane is coincident with the origin of coordinate system 42.

Figure 3:
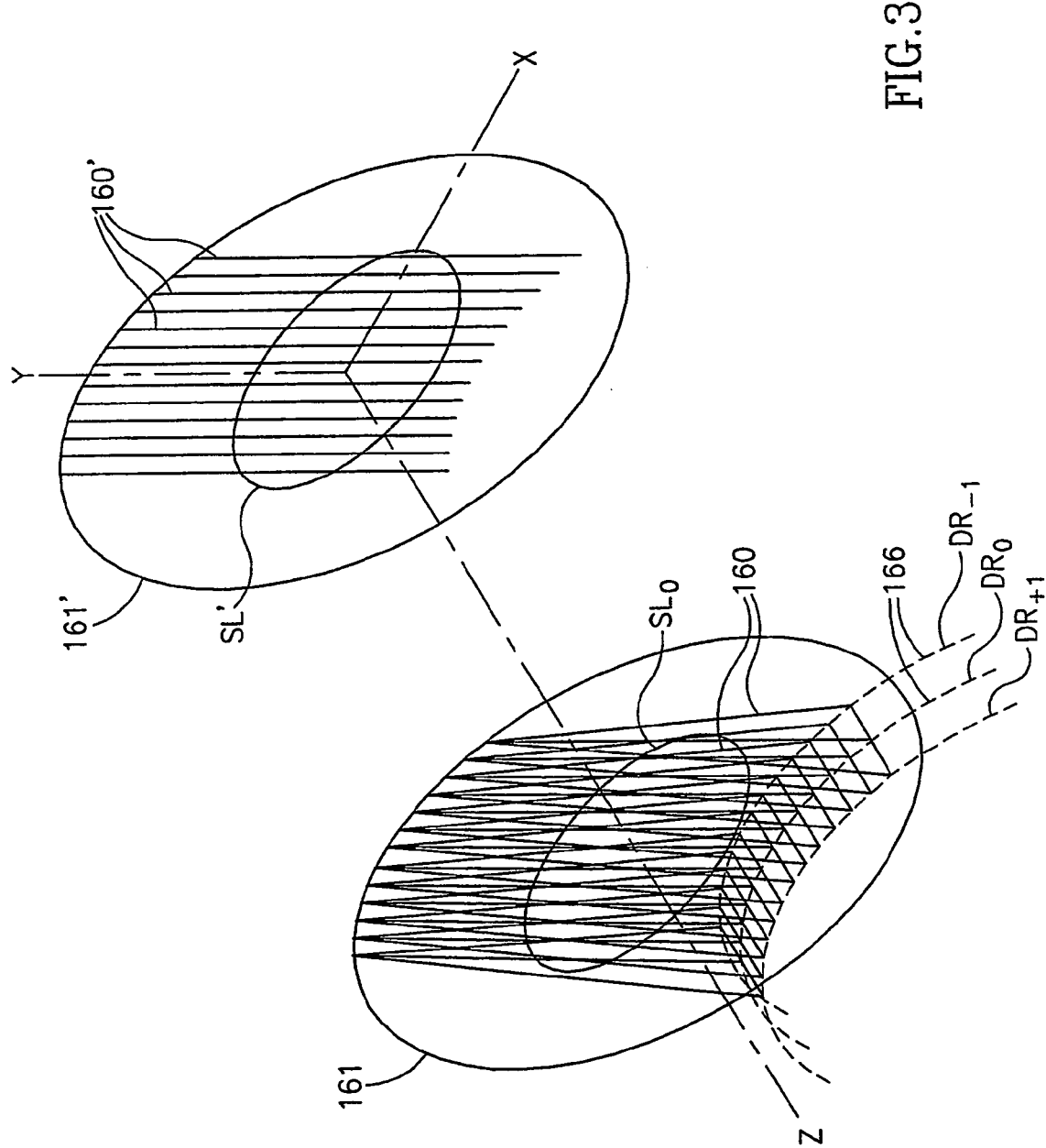
FIG. 3 schematically shows attenuation paths for a cone beam parallel view at a view angle of 0° acquired by the CT scanner shown in FIG. 1.

FIG. 3 schematically shows attenuation paths 160 for a cone beam parallel view of region 122 at a view angle of 0° and projections 160' of the paths and projection SL' of ellipse $SL_0$ on the xy-plane. Circle 161 lies in midplane $MP_0$ (FIG. 1) of cone beam 138 and indicates a circle around which focal spot 136 moves as cone beam 138 rotates around isocenter 144 to acquire a cone beam views of region 122 at a plurality of cone beam view angles. Circle 161' is a projection of circle 161 on the x-y plane. In the 0° parallel cone beam view, to moderate clutter, only ellipse $SL_0$ that lies on midplane $MP_0$ (FIG. 1) is shown. To aid in visualization, a dashed line 166 connects all attenuation paths 160 defined by detectors 132 in a same row 128 (FIGS. 4 and 5) of detectors 132. Each dashed line 166 is labeled with the label of the detector row 128 that defines attenuation paths 160 that are connected by the dashed line. A parallel view for a particular row 128 of detectors 132 comprises line integrals for all attenuation paths connected by the dashed line 166 corresponding to the row of detectors. For example, for the 0° cone beam parallel view shown in FIG. 3, the parallel view at 0° defined by detector row $DR_1$ comprises line integrals for attenuation paths connected by dashed line $DR_1$.

Figure 4:
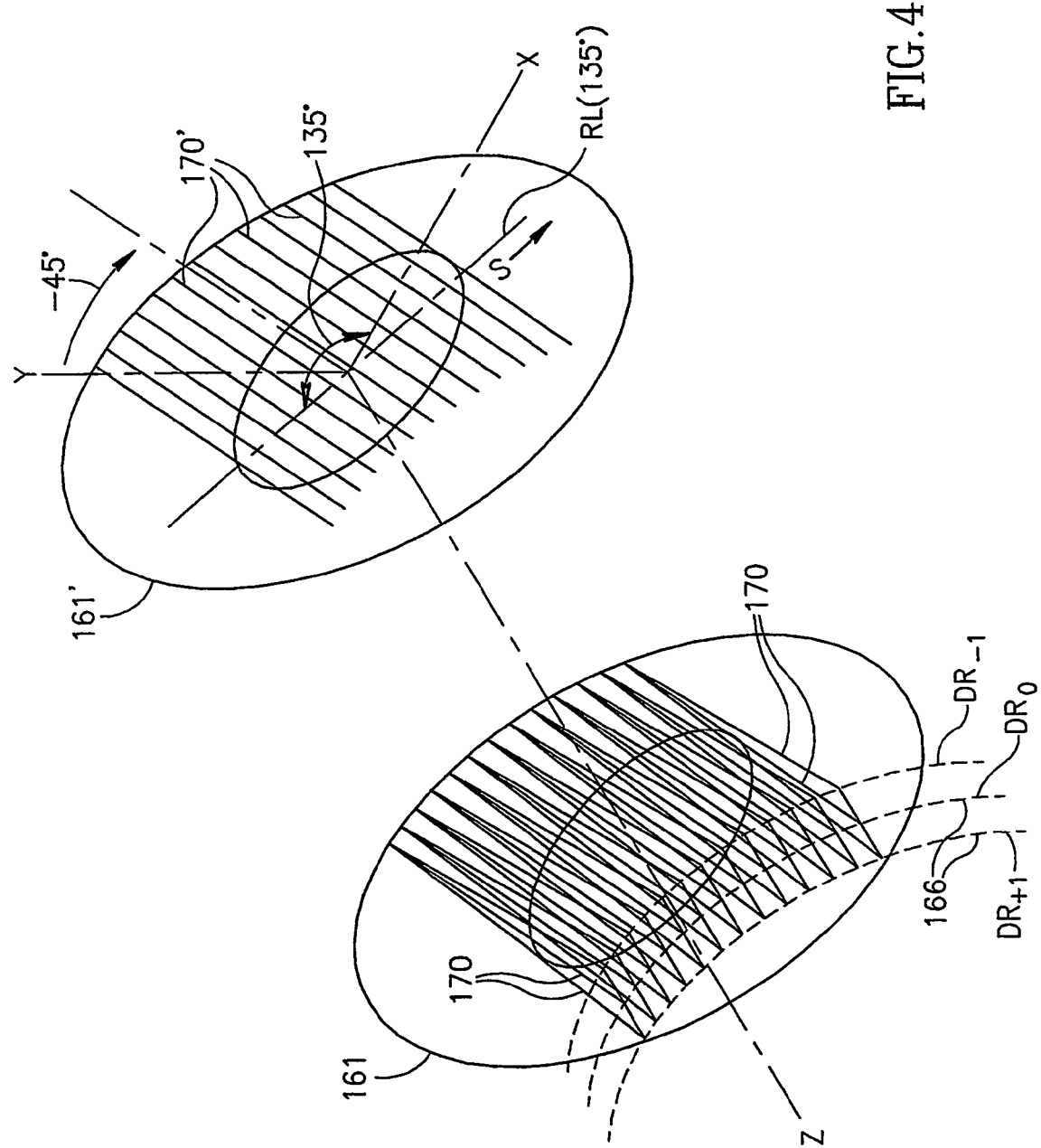
FIG. 4 schematically shows attenuation paths for a cone beam parallel view at a view angle of 315° (−45°) acquired by the CT scanner shown in FIG. 1.

FIG. 4 is similar to FIG. 3, but schematically shows attenuation paths 170 and their respective projections 170' for a parallel cone beam view at 315° (i.e. −45° in FIG. 4, rotation is positive in the counterclockwise direction about the z-axis).

Figure 5:
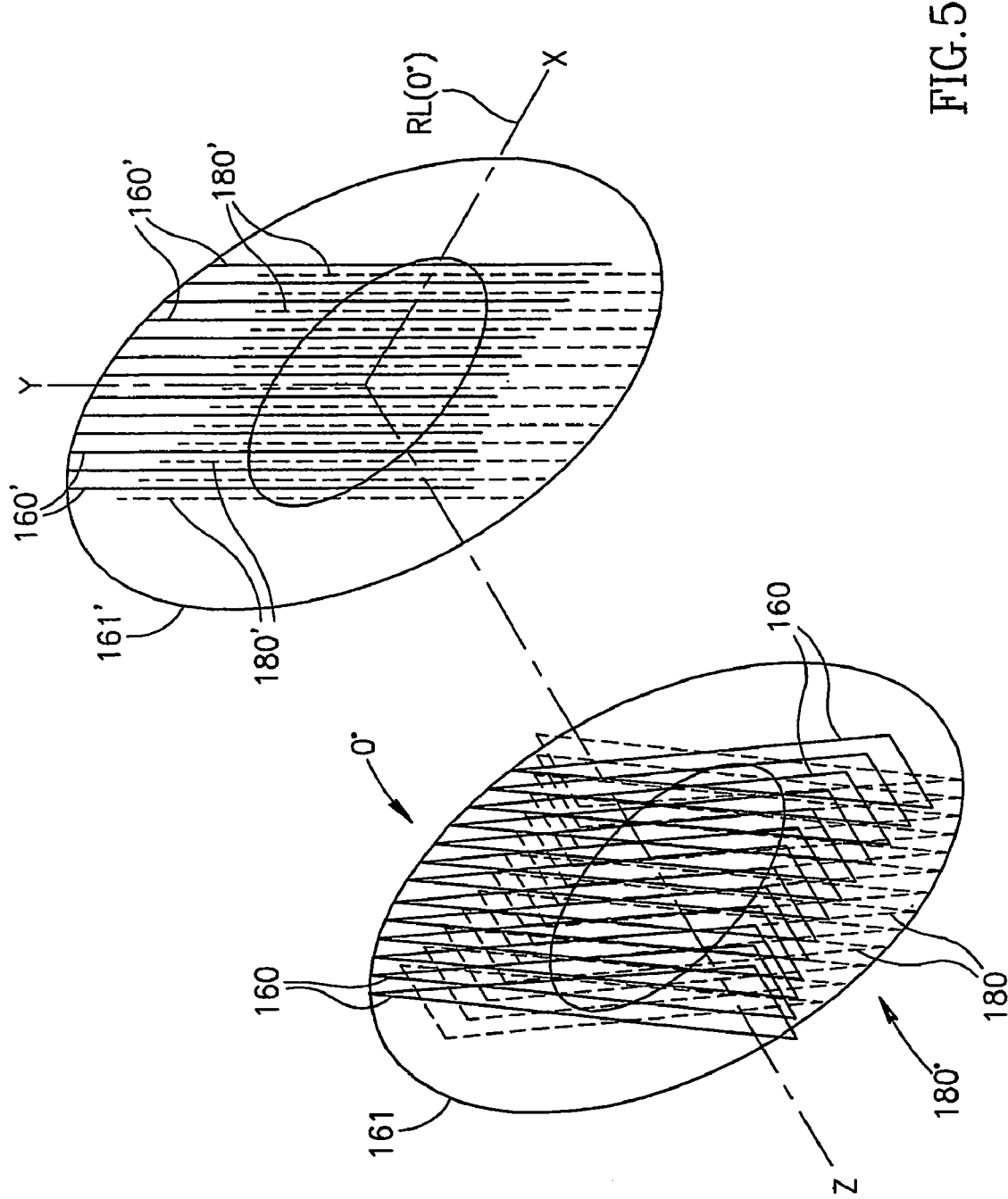
FIG. 5 schematically shows attenuation paths for a cone beam parallel view at a view angle of 0° acquired by the CT scanner shown in FIG. 1 interleaved with attenuation paths of a parallel view at a view angle 180° acquired by the scanner.

FIG. 5 schematically shows attenuation paths 180, shown in dashed lines, for a cone beam parallel view at 180° superposed on attenuation paths 160, shown in solid lines, for the 0° cone beam parallel view shown in FIG. 3. Projections 160' of attenuation paths 160 and projections 180' of attenuation paths 180 on the xy-plane are also shown. Because cone beam 138 is offset rotated, projections 180' are not coincident with the projections 160' and instead "interleave" projections 160'.

Let a parallel view at a view angle φ for a detector row $DR_r$ (r being the subscript that denotes a particular row 128 shown in FIG. 1) be represented by PV(φ,r,s). Each parallel view PV(φ,r,s) comprises a set of samples at different discrete values of s for a Radon function $R_{φ'}(r,s)$, where 0°≦φ'<180°, and φ'=φ mod 180°. Each parallel view PV(φ,r,s) comprises a number of samples for an associated Radon function $R_{φ'}(r,s)$ equal to a number of detectors 132 in its associated detector row $DR_r$. The argument s represents distance from isocenter 144 of a projection onto midplane $MP_0$ (FIG. 1) of cone beam 138 of an attenuation path belonging to PV(φ,r,s). (In accordance with the convention that projections onto midplane $MP_0$ are projections onto the xy-plane, s is the distance of the projection of the attenuation path on the xy-plane from projection 144' of isocenter 144'). The distance s is measured along a line, hereinafter referred to as a "Radon line", "RL(φ')" that is perpendicular to the projection and passes through isocenter 144 at the angle φ' with respect to the x-axis.

FIG. 4 shows the Radon line RL(135°) (135°=315° mod 180°) for the parallel views PV(315°,−1,s), PV(315°,0,s) and PV(315°,1,s) comprised in parallel cone beam view at view angle 315° shown in the figure. The s coordinates of PV(315°,r,s) are the s coordinates of the intersections of projections 170' with Radon line RL(135°). In FIG. 5 the common Radon line RL(0°) for cone beam parallel views at view angles 0° and 180° is coincident with the x-axis and the x-axis is therefore also labeled RL(0°) To determine values for the absorption coefficient of voxels in region 122 that are illuminated by X-rays in cone beam 138, each parallel view PV(φ,r,s) is interpolated to replace the original set of line integrals that it contains with a set of line integrals evaluated at equally spaced values of s along the parallel view's Radon line RL(φ'). Let spacing between equally spaced values of the s-coordinate for which line integrals are interpolated be represented by Δs. Hereinafter, it is assumed that the line integrals in a parallel view PV(φr,s) are appropriately interpolated at equally spaced values of s.

Figure 6:
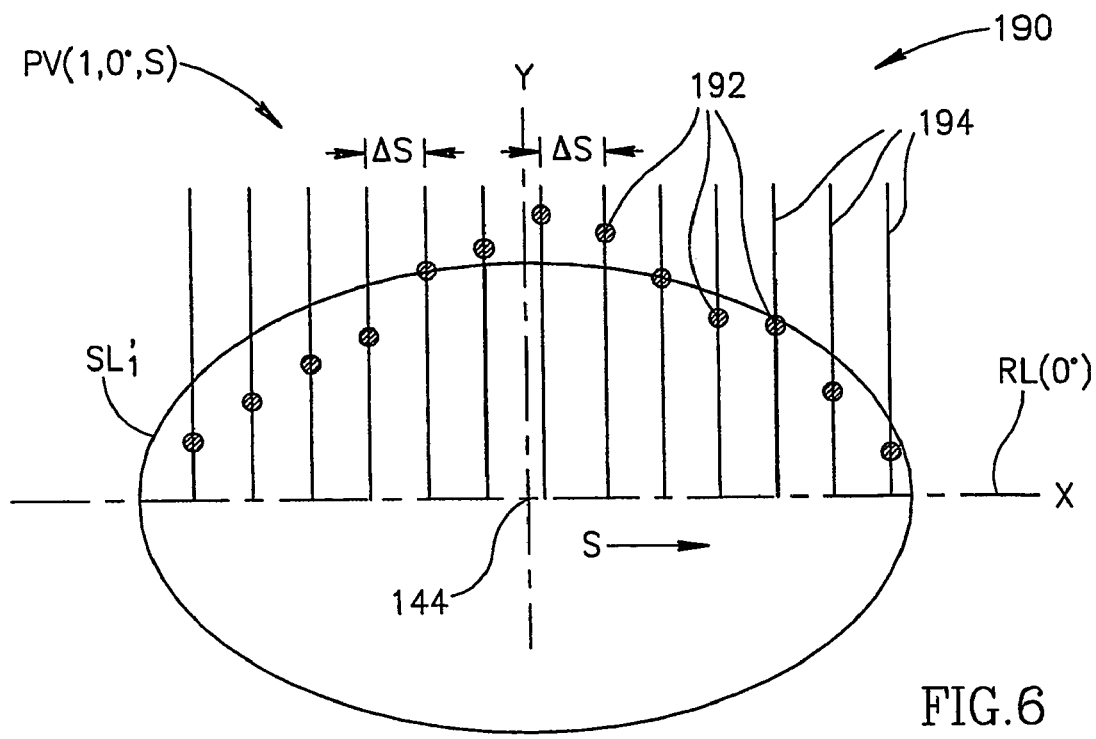
FIG. 6 shows a schematic graph of line integral values for attenuation paths of the 0° cone beam parallel view shown in FIG. 3.

FIG. 6 shows a schematic graph 190 of interpolated line integral values indicated by shaded circles 192 for a parallel view PV(φ,r,s) for φ=0°, r=1 and for s coordinates along Radon line RL(0°) shown in FIG. 5, which is coincident with the x-axis. For orientation, a projection $SL'_1$ of slice $SL_1$ (FIG. 1) is shown on graph 190. Values of line integrals for the parallel view PV(0°,1,s) are indicated with shaded circles 192 for s coordinates that are intersection points of lines 194 with the x-axis. Lines 194 schematically represent attenuation paths that pass through slice $SL_1$ at distances s from isocenter 144 for which interpolated line integral values 192 are determined. Isocenter 144 coincides with the origin of the x and y axis of graph 190.

In some prior art methods for generating an image of region 122 from "interpolated line integral data" acquired by scanner 120 the data is processed using any of various 2D or 3D filtered back projection algorithms.

By way of example, for a "low resolution image" of region 122, in accordance with some prior art 3D filtered back projection schemes, each interpolated parallel view PV(φ,r,s) is Fourier transformed to provide a Fourier transform "$FR_{φ'}(φ,r,ω)$" of the Radon function $R_{φ'}(r,s)$ where, $$FR_{φ'}(\varphi, r, \omega) = \int_{-\infty}^{\infty} PV(\varphi, r, s)\exp(-i\omega s)ds.$$

(Whereas a parallel view PV(φ,r,s) is a discrete set of data and integration of a parallel view is performed by summing, for convenience of presentation, integrals are used rather than sums.) Each function $FR_{φ'}(φ,r,ω)$ is generally multiplied by the "Jacobian" filter |ω| and inverse Fourier transformed to provide a "filtered Radon function"

$$R^*_{φ'}(\varphi, r, s) = \int_{-\omega_N}^{\omega_N} FR_{φ'}(\varphi, r, \omega)\exp(i\omega s)|\omega|d\omega,$$

where $ω_N$ is a Nyquist frequency that band limits the function $FR_{φ'}(φ,r,ω)$. The Nyquist frequency is approximately equal to 1/(2Δs). Spacing Δs is proportional to a number of samples in each parallel view PV(r,φ,s), which is substantially equal to a number "N" of detectors in a row 128 of detectors. (The filtered Radon function at angle (φ', $R^*_{φ'}(φ,r,s)$ has φ as an argument because as noted above, φ'=φ mod 180°. Therefore, there are two filtered Radon functions $R^*_{φ'}(φ,r,s)$ for each angle φ', one generated from the interpolated parallel view PV(φ,r,s) and one generated from the interpolated parallel view PV(φ+180°,r,s)).

In the above discussion, a Radon function $R_{φ'}(r,s)$ and its Fourier transform $FR_{φ'}(φ,r,ω)$ are defined for a specific single value of r and that samples for the Radon function are acquired from parallel views PV(φ,r,s) having a same value of r as the Radon function. However, it is noted that a Radon function may be defined by samples provided by a plurality of parallel views PV(φ,r,s) having different values of r, i.e.

a Radon function may be defined by samples provided by a plurality of detector rows 128 (FIG. 1). For simplicity of presentation it is assumed that a Radon function is defined for a specific value of r and that its Fourier transform is defined by the integral noted at the beginning of the preceding paragraph.

For helical scan data, the functions $R^*_{\phi'}(\phi,r,s)$ that are used to determine a value for the absorption coefficient of a voxel located at coordinates (x, y, z) in region 122 are limited to a span of about 180°, i.e. for the functions $R^*_{\phi'}(\phi,r,s)$ that are used to determine a value for the absorption coefficient ($\phi_L < \phi < \phi_U$ where ($\phi_U - \phi_L$) is equal to about 180°. The limitation to a span of about 180° is generally made to moderate "discordance" in the data caused by lack of coplanarity of views acquired in the scan and thereby possible image artifacts generated by such discordance. Each function $R^*_{\phi'}(\phi,r,s)$ is defined by samples from a single parallel view for which $\phi = \phi'$. The filtered Radon function $R^*_{\phi'}(\phi',r,s)$ for the helical scan is therefore a low sampling rate function limited by the Nyquist frequency $\phi_N$ that is determined by a number of samples in the single parallel view, i.e. the number of detectors 128 in a row 132 of detectors.

The functions $R^*_{\phi'}(\phi',r,s)$ are generally interpolated responsive to the coordinates of the voxel using any of various 2D back-projection or 3D back-projection methods known in the art to define a function of angle $\phi'$, $R^*(\phi',x,y,z)$, for the coordinates (x,y,z). If the absorption coefficient of the voxel is represented by $\rho(x,y,z)$, then $\rho(x,y,z)$ is determined by back projecting $R^*(\phi',x,y,z)$ in accordance with a relationship $$\rho(x, y, z) = \int_0^\pi R^*(\varphi', x, y, z) d\varphi'.$$

Limiting view angles used to determine each absorption coefficient $\rho(x,y,z)$ to a span of about 180°, tends to moderate artifacts in an image provided from the absorption coefficients that are generated by lack of coplanarity, "i.e. discordance", of views acquired by cone beam 138.

For an axial scan, the functions $R^*_{\phi'}(\phi,r,s)$ that are used to determine a value for the absorption coefficient of a voxel located at coordinates (x, y, z) in region 122 are limited to a span of about 360°, i.e. for the functions $R^*_{\phi'}(\phi,r,s)$ that are used ($p_L < \phi < \phi_U$ where ($\phi_U - \phi_L$) is about 360°. Each function $R^*_{\phi'}(\phi,r,s)$ is generally interpolated responsive to the coordinates of the voxel using any of various methods known in the art to define a function of angle $\phi'$ and $\phi$, $R^*(\phi',\phi,x,y,z)$, for the coordinates (x,y,z). The functions $R^*(\phi',\phi,x,y,z)$ are used to determine a function $R^*(\phi,x,y,z)$. In order to moderate image artifacts that may arise due to the one beam angle a value for the function $R^*(\phi',x,y,z)$ for a given value of $\phi'$ and given values for the spatial coordinates (x,y,z) is determined from a weighted average of $R^*(\phi',\phi,x,y,z)|_{\phi=\phi'}$ and $R^*(\phi',\phi,x,y,z)|_{\phi=(\phi'+180°)}$.

It is noted that even though for the axial case $R^*(\phi',x,y,z)$ is defined using parallel views in a 360° view angle span, $R^*(\phi',x,y,z)$ remains a "low frequency function" limited by the Nyquist frequency $\phi_N$, since the sampling frequency of each of the functions $R^*(\phi',\phi,x,y,z)$ is about $1/(2\Delta s)$. As in the case for the helical mode $\rho(x,y,z)$ is determined from $R^*(\phi',x,y,z)$ in accordance with the expression $$\rho(x, y, z) = \int_0^\pi R^*(\varphi', x, y, z) d\varphi'.$$

A resolution of an image generated from values of $\rho(x,y,z)$ is a function of the band limiting Nyquist frequency $\omega_N$. To an extent that $\omega_N$ is larger, resolution of an image of region 122 improves. In prior art, to increase a sampling rate and thereby increase CON and improve a resolution of an image of region 122, data from each parallel view $PV(\phi,r,s)$ and its "companion" parallel view $PV(\phi+180°,r,s)$ are combined to provide a "high sampling rate" set of line integrals for each Radon function $R_{\phi'}(r,s)$.

Since, optionally, cone beam 138 is offset rotated, s coordinates along a Radon line $RL(\phi')$ for a parallel view $PV(\phi,r,s)$ are located between and equidistant from adjacent s coordinates along Radon line $RL(\phi')$ for a "companion" parallel view $PV(\phi+180°,r,s)$. The line integrals for a parallel view $PV(\phi,r,s)$ are "interleaved" with the line integrals for a companion view $PV(\phi+180°,r,s)$. The parallel view $PV(\phi,r,s)$ together with its companion parallel view $PV(\phi+180°,r,s)$, when combined, provide twice as many samples and thereby double a sampling rate for the Radon function $R_{\phi}(r,s)$ as does either parallel view alone.

Figure 7:
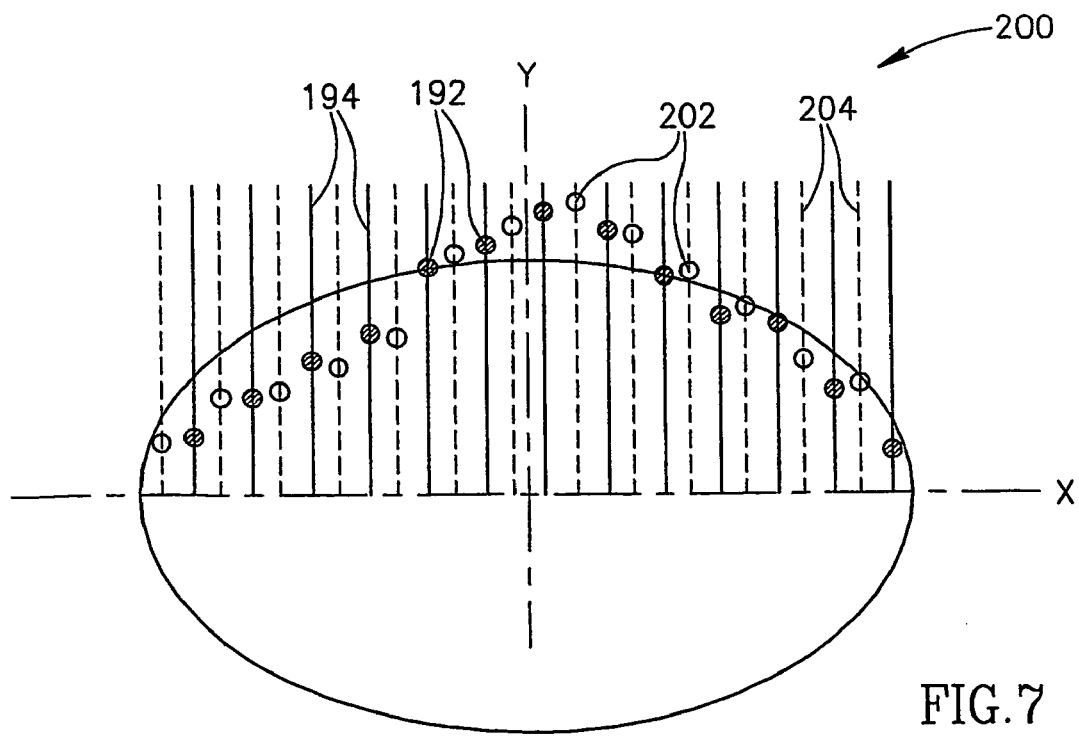
FIG. 7 shows a schematic graph of line integral values for interleaved attenuation paths at 0° and 180° shown in FIG. 5

By way of example, FIG. 7 shows a schematic graph 200 of line integral values for parallel view $PV(0°,1,s)$ shown in FIG. 6 together with "interleaved" line integral values for the companion parallel view $PV(180°,1,s)$. Values of line integrals for the parallel view $PV(180°,1,s)$ are shown with un-shaded circles 202 for values of s coordinates at intersection points of dashed lines 204 with the x-axis.

Let the combined set of line integrals from a parallel view $PV(\phi,r,s)$ and its companion 180° parallel view $PV(\phi+180°,r,s)$ be referred to as a high resolution parallel view at angle $\phi$ and let the high resolution parallel view be represented by "$HPV(\phi,r,s)$". For both helical and axial scans, the sets of high resolution parallel views $HPV(\phi,r,s)$ are generally processed similarly to the manner in which low resolution parallel views $PV(\phi,r,s)$ generated from helical or axial scan data are processed to provide values for the absorption coefficient $\rho(x,y,z)$ of region 122.

Each function $HPV(\phi,r,s)$ is Fourier transformed to provide a high resolution Fourier transform "$FR_{h\phi}(,r,\omega)$" of the Radon function $R_\omega(r,s)$, where $$FR_{h\varphi}(, r, \omega) = \int_{-\infty}^{\infty} HPV(r, \varphi, s) \exp(-i\omega s) ds.$$

The function $FR_{h\phi}(,r,\omega)$ is band limited by a Nyquist frequency equal to about $2\omega_N$ rather than $\omega_N$ because each high resolution parallel view $HPV(\phi,r,s)$ comprises about twice the number of samples as each low resolution parallel view $PV(\phi,r,s)$. Each function $FR_{h\phi}(r,\omega)$ is filtered to provide a high resolution filtered Radon function $$R^*_{h\varphi}(r, s) = \int_{-2\omega_N}^{2\omega_N} FR_{h\varphi}(r, \omega) \exp(i\omega s) |\omega| d\omega.$$

For a voxel at coordinates (x, y, z), for each angle $\phi$ the functions $R^*_{h\phi}(r,s)$ are processed to define a high resolution function $R^*_{h\phi}(x,y,z)$ and therefrom a high resolution value $\rho_h(x,y,z)$ for the absorption coefficient of the voxel where $$\rho_h(x, y, z) = \int_0^\pi R^*_{h\varphi}(x, y, z) d\varphi.$$

However, a parallel view $PV(\phi,r,s)$ and its 180° companion parallel view $PV(\phi+180°,r,s)$ that are used to provide a high frequency parallel view $HPV(\phi,r,s)$ are generally not coplanar (companion views are coplanar only for midplane views in an axial scan) and do not in actuality comprise samples of a same Radon function. As a result, an image, in accordance with prior art, of region 122 provided from $\rho_h(x,y,z)$ generally comprises an unsatisfactory level of artifacts.

In accordance with an embodiment of the present invention, to reduce artifacts and provide a high frequency image of region 122 an image of region 122 is provided by generating low frequency and high frequency "partial" images of the region and combining the two.

For the low frequency image, each parallel view $PV(\phi,r,s)$ is Fourier transformed to provide a Fourier transform $FR_{\phi'}(\phi,r,\omega)$ of the Radon function $R_\phi(r,s)$ at angle $\phi'$, where as in prior art $$FR_{\varphi'}(\varphi, r, \omega) = \int_{-\infty}^\infty PV(\varphi, r, s) \exp(i\omega s) ds$$

(noting again that $\phi' = \phi \bmod 180°$). A low frequency filtered Radon function "$LR^*_{\phi'}(\phi,r,s)$", in accordance with an embodiment of the present invention, is then determined optionally using a low frequency filter $f_L(\omega)$ in accordance with an equation, $$LR^*_{\varphi'}(\varphi, r, s) = \int_{-\omega_N}^{\omega_N} FR_{\varphi'}(\varphi', r, \omega) \exp(i\omega s) |\omega| f_L(\omega) d\omega.$$

Low frequency filter $f_L(\omega)$ has non-zero values for $\omega$ less than $\omega_N$ and is equal to substantially zero for values of $\omega$ greater than $\omega_N$. Optionally $f_L(\omega)$ is equal to substantially one for values of $\omega$ substantially less than $\omega_N$. The filter $f_L(\omega)$, optionally adiabatically, decreases to zero at a value for $\omega$, which is less than $\omega_N$, in a neighborhood of $\omega_N$.

For helical scan data, functions $LR^*_{\phi'}(\omega,r,s)$ that are used, in accordance with an embodiment of the present invention, to determine a value for the absorption coefficient of a voxel located at coordinates (x, y, z) in region 122 are limited to a span of about 180°, i.e. $\phi_L < \phi < \phi_U$ where $(\phi_U - \phi_L)$ is equal to about 180° and have $\phi = \phi'$. For a voxel located at coordinates (x, y, z) in region 122, for each angle $\phi'$, the functions $LR^*_{\phi'}(\phi',r,s)$ are interpolated responsive to the coordinates of the voxel using any of various methods known in the art to define a function $LR^*(\phi',x,y,z)$ and a low frequency absorption coefficient $\rho_L(x,y,z)$ is determined for the voxel, where $$\rho_L(x, y, z) = \int_0^\pi LR^*(\varphi', x, y, z) d\varphi'.$$

For an axial scan, the functions $LR^*_{\phi'}(r,\phi,s)$ that are used to determine a value for the absorption coefficient of a voxel located at coordinates (x, y, z) in region 122 are limited to a span of about 360°, i.e. $\phi_L < \phi < \phi_U$ where $(\phi_U - \phi_L)$ is about 360°. Each function $LR^*_{\phi'}(r,\phi,s)$ is interpolated responsive to the coordinates of the voxel using any of various methods known in the art to define a function of angle $\phi'$ and $\phi$, $LR^*(\phi',\phi,x,y,z)$, for the coordinates (x,y,z). The functions $LR^*(\phi',\phi,x,y,z)$ are used to determine a function $LR^*(\phi',x,y,z)$. A value for the function $LR^*(\phi',x,y,z)$ for a given value of $\phi'$ and given values for the spatial coordinates x,y,z is optionally determined from a weighted average of $LR^*(\phi',\phi,x,y,z)|_{\phi=\phi'}$ and $R^*(\phi',\phi,x,y,z)|_{\phi=(\phi'+180°)}$. The function $LR^*(\phi',x,y,z)$ is used to determine $\rho_L(x,y,z)$ as above with $$\rho L(x, y, z) = \int_0^\pi LR * (\varphi', x, y, z) d\varphi'.$$

The absorption coefficients $\rho_L(x,y,z)$ for voxels at different locations in region 122 are used, in accordance with an embodiment of the present invention, to generate a low frequency image "$IM_L(x,y,z)$" of the region. For helical scan data the low frequency image is generally relatively free of artifacts because each of the parallel views used to determine $\rho_L(x,y,z)$, in accordance with an embodiment of the present invention, is provided from a span of view angles substantially less than 360° and optionally to a span of view angles about equal to 180°. For axial scan data the low frequency image is generally relatively free from artifacts as a result of the weighting procedure used to combine data from companion views to determine $LR^*(\phi',x,y,z)$.

For the high frequency image, for an axial or helical scan, to determine a value for the absorption coefficient of a voxel located at coordinates (x, y, z) in region 122 a high frequency parallel view, $HPV(\phi',r,s)$ is defined for each view angle $\phi'$ in a span of 180°. The high frequency parallel view $HPV(\phi',r,s)$ comprises a set of line integrals from a parallel view $PV(\phi',r,s)$ and its companion 180° parallel view $PV(\phi'+180°,r,s)$. (It is noted that in accordance with an embodiment of the present invention, data from a view angle span of about 360° is used to generate the functions $HPV(\phi',r,s)$.) Each function $HPV(\phi',r,s)$ is Fourier transformed to provide a high frequency Fourier transform "$HFR_{\phi'}(r,\omega)$" of the Radon function $R_{\phi'}(r,s)$, where $$HFR_{\varphi'}(r, \omega) = \int_{-\infty}^\infty HPV(\varphi, r, s) \exp(-i\omega s) ds.$$

A high frequency filtered Radon function "$HR^*_{\phi'}(r,s)$", in accordance with an embodiment of the present invention, is then determined from each Fourier transform $HFR_{\phi'}(r,\omega)$ optionally using a "high-frequency" filter $f_H(\omega)$. In symbols, high frequency filtered Radon function $HR^*_{\phi'}(r,s)$ is defined by the equation, $$HR *_{\varphi'} (r, s) = \int_{-2\omega_N}^{2\omega_N} HFR_{\varphi'}(r, \omega) \exp(i\omega s) |\omega| f_H(\omega) d\omega.$$

High frequency filter $f_H(\omega)$ is equal substantially to zero for values of $\omega$ substantially less than $\omega_N$ and values of $\omega$ greater than $2\omega_N$. Optionally $f_H(\omega)$ is substantially equal to one for values of $\omega$ in a neighborhood of $\omega_N$. Optionally $f_H(\omega)$ decreases adiabatically to zero at a value $\omega$ less than $\omega_N$. Optionally $f_H(\omega)$ decreases adiabatically to zero at a value ω in a neighborhood of $2ω_N$. Optionally, the functions $f_H(ω)$ and $f_L(ω)$ are related by an expression $f(ω)=f_H(ω)+f_L(ω)$ where $f(ω)$ is equal substantially to one for values of ω substantially less than $ω_N$ and equal to substantially zero for ω greater than $2ω_N$. Optionally, $f(ω)$ is equal substantially to one for values of ω in a neighborhood of $ω_N$. Optionally, $f(ω)$ decreases adiabatically to zero at a value of ω less than and in a neighborhood of $2ω_N$.

For the voxel located at coordinates (x, y, z), for each angle φ', the functions $HR*_{φ'}(r,s)$ are interpolated with respect to variables r and/or s responsive to the coordinates of the voxel using any of various methods known in the art to define a high frequency function of φ', $HR*(φ',x,y,z)$. A high frequency value "$ρ_H(x,y,z)$" for the absorption coefficient of the voxel is determined in accordance with the expression $$ρH(x, y, z) = \int_0^π HR*(φ', x, y, z)dφ'.$$

Figure 8A:
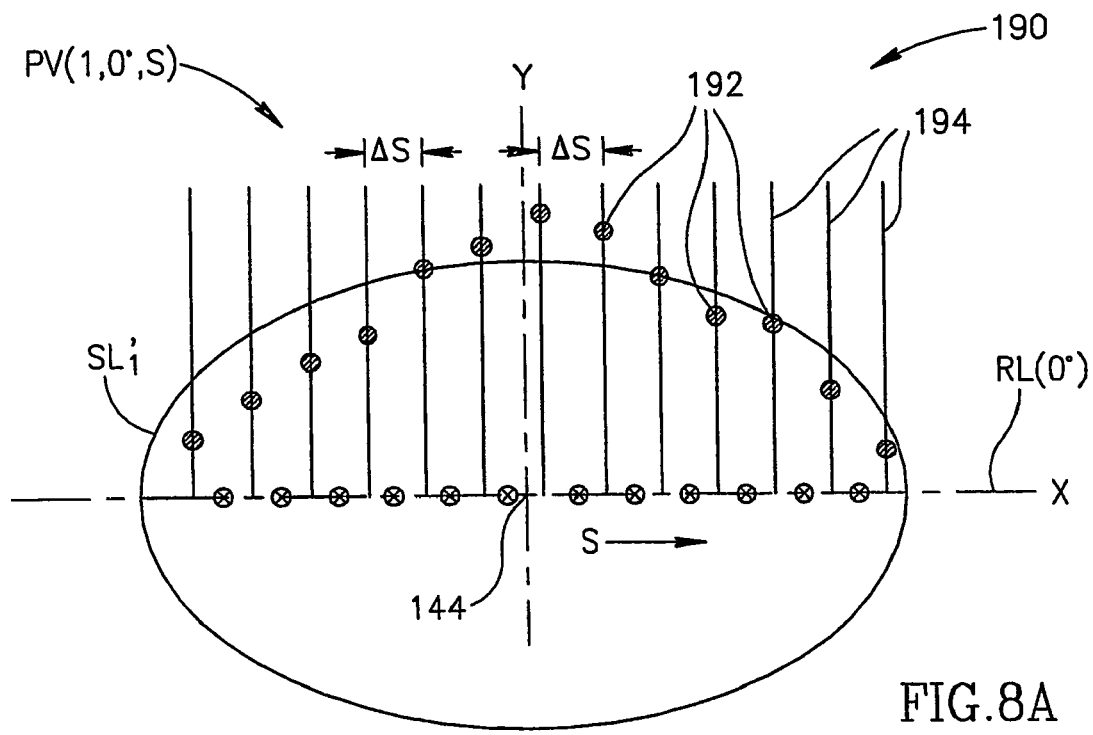
FIGS. 8A and 8B schematically show high sampling rate parallel views at 0° and 180°, in accordance with an embodiment of the present invention.
Figure 8B:
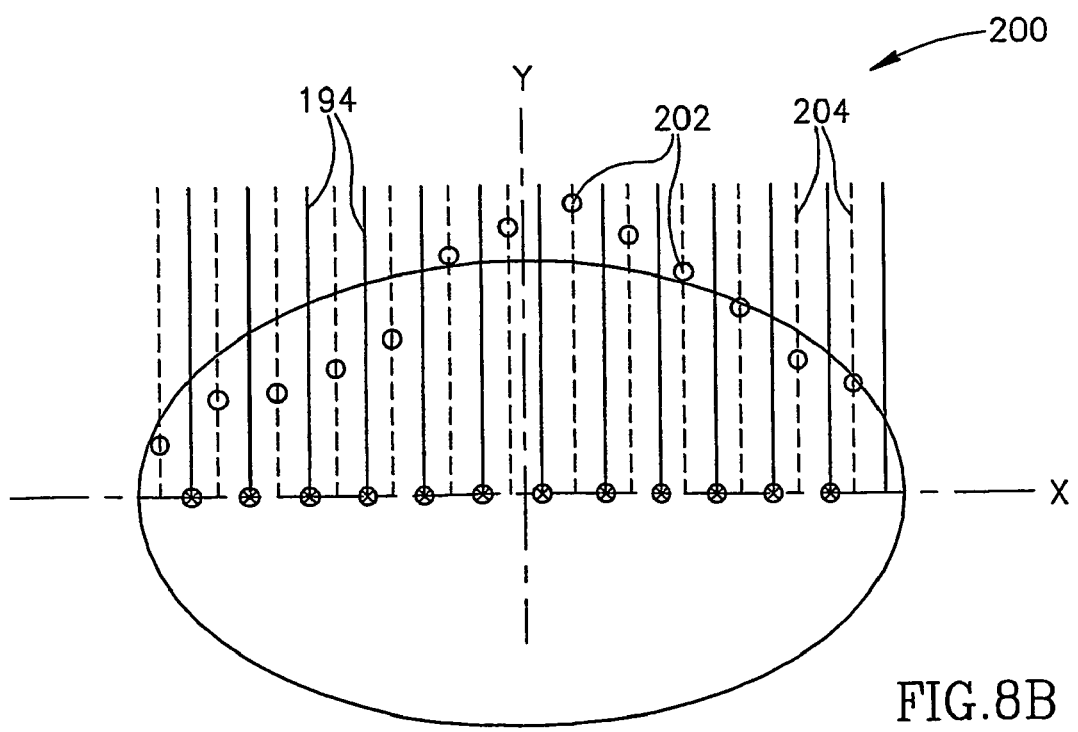

In some embodiments of the present invention, for a voxel at coordinates (x, y, z) each parallel view PV(φ,r,s) in a 360° span of parallel view is converted into a high sampling rate parallel view by padding the parallel view with dummy, null value line integrals. A dummy line integral is added at each s value for which a companion view at (φ+180°) to the view at φ provides a line integral so that the dummy line integrals are interleaved with the real line integral values of the view at φ. By way of example, FIG. 8A shows a schematic graph 210 of line integral values 192 for parallel view PV(0°,1,s), which are shown in FIG. 6, padded, in accordance with an embodiment of the present invention with dummy null value line integrals 212 indicated by circles enclosing an "X". FIG. 8B shows a schematic graph 214 of line integral values 202 for parallel view PV(180°,1,s) which are shown in FIG. 7, padded with dummy value line integrals 216 in accordance with an embodiment of the present invention. Each padded parallel view is separately processed similarly to the manner in which each high frequency parallel view HPV(φ,r,s) discussed above is processed.

Let a padded parallel view, in accordance with an embodiment of the present invention, be represented by PPV(φ,r,s). Each function PPV(φ,r,s) is Fourier transformed to provide a high frequency Fourier transform "$PFR_φ(r,ω)$" of the Radon function $R_φ(r,s)$, where $$PFR_{φ'}(φ, r, ω) = \int_{-∞}^{∞} PPV(r, φ, s)\exp(-iωs)ds$$

(and as usual φ=φ' or φ'+180°). The function $PFR_φ(φ,r,ω)$ is then filtered using the high frequency filter $f_H$ to generate a filtered "padded" Radon function $PR*_{φ'}(φ,r,s)$, where $$PR*_{φ'}(φ, r, s) = \int_{-2ω_N}^{2ω_N} PFR_{φ'}(φ, r, ω)\exp(iωs)|ω|f_H(ω)dω.$$

As above, the functions $PR*_{φ'}(φ,r,s)$ are interpolated with respect to variables r and/or s responsive to the coordinates (x, y, z) of the voxel using any of various methods known in the art to define a high frequency function of φ', $PR*_{φ'}(φ,x,y,z)$. A high frequency filtered Radon function $HR*_{φ'}(r,s)$ is defined by adding functions generated from companion parallel views at view angles φ' and (φ'+180°). In symbols $HR*(φ'x,y,z)=(PR*_{φ'})(φ',x,y,z)+PR*_{φ'}(φ'+180°, x,y,z))$. The functions $HR*(φ',x,y,z)$ are then integrated to determine the absorption coefficient for the voxel in accordance with the expression $$ρH(x, y, z) = \int_0^π HR*(φ', x, y, z)dφ'.$$

It is noted that the use of padded companion parallel views, in accordance with an embodiment of the present invention, for determining a high frequency filtered Radon function $HR*_{φ'}(r,s)$ is possible, because all the steps involved in generating a filtered Radon function are linear. The inventors have found that it can be computationally simpler to pad views with zeros before filtering and combine data from companion views after filtering rather than combine data from companion views before filtering. For 3D back-projection schemes, first combining data from companion views PV(φ,$r_i$,s) and PV(φ+180°,$r_j$,s) for different combinations of {$r_i$,$r_j$} and then filtering the combined data generally requires massive computational effort due to a very large number of possible combinations for {$r_i$,$r_j$}.

The absorption coefficients $ρ_H(x,y,z)$ for voxels at different locations in region 122 are used, in accordance with an embodiment of the present invention, to generate a high frequency image "$IM_H(x,y,z)$" of the region. The high frequency image is generally relatively free of artifacts because, high frequency components of the Fourier transform of the absorption coefficient generated from parallel views comprising data from view angle spans of about 360° do not generally generate artifacts.

A high resolution image "$IM_{HR}(x,y,z)$" for region 122 relatively free of artifacts is provided, in accordance with an embodiment of the present invention, from the low frequency image $IM_L(x,y,z)$ and the high frequency image $IM_H(x,y,z)$, where $IM_{HR}(x,y,z)$ is defined by an equation $IM_{HR}(x,y,z)=IM_L(x,y,z)+αIM_H(x,y,z)$. In the expression for $IM_{HR}(x,y,z)$ α is a weighting factor that determines how much of the high spatial frequencies contribute to $IM_{HR}(x,y,z)$ and thereby a sharpness and resolution of the image $IM_{HR}(x,y,z)$. In accordance with an embodiment of the present invention, the weighting factor α is adjusted in real time during imaging of a region of a patient to increase or decrease sharpness of the image.

Whereas the above exemplary methods for processing cone beam data, in accordance with an embodiment of the present invention, employ 3D back projection, practice of the present invention is not limited to algorithms that employ 3D back projection. For example, the inventor has found that as a cone angle of a cone beam increases, 2D back projection methods for processing cone beam data that combine 180° companion views to provide high resolution images tend to generate more artifacts in the images. Artifacts in a high resolution image of a region generated by a "high resolution" 2D back projection algorithm can be mitigated, in accordance with an embodiment of the present invention, by generating low and high frequency partial images of the region using the 2D back projection algorithm. The high and low frequency partial images are then combined, in accordance with an embodiment of the present invention, to provide a high resolution image. As in the exemplary methods discussed above, the low frequency partial image is generated from parallel views comprising data from view angle spans of about 180° for helical scan data and by averaging data from companion views in a view angle span of about 360° for axial scan data. The high frequency partial image is generated from companion views combined to provide parallel views comprising data from view angle spans of about 360°.

Figure 9:
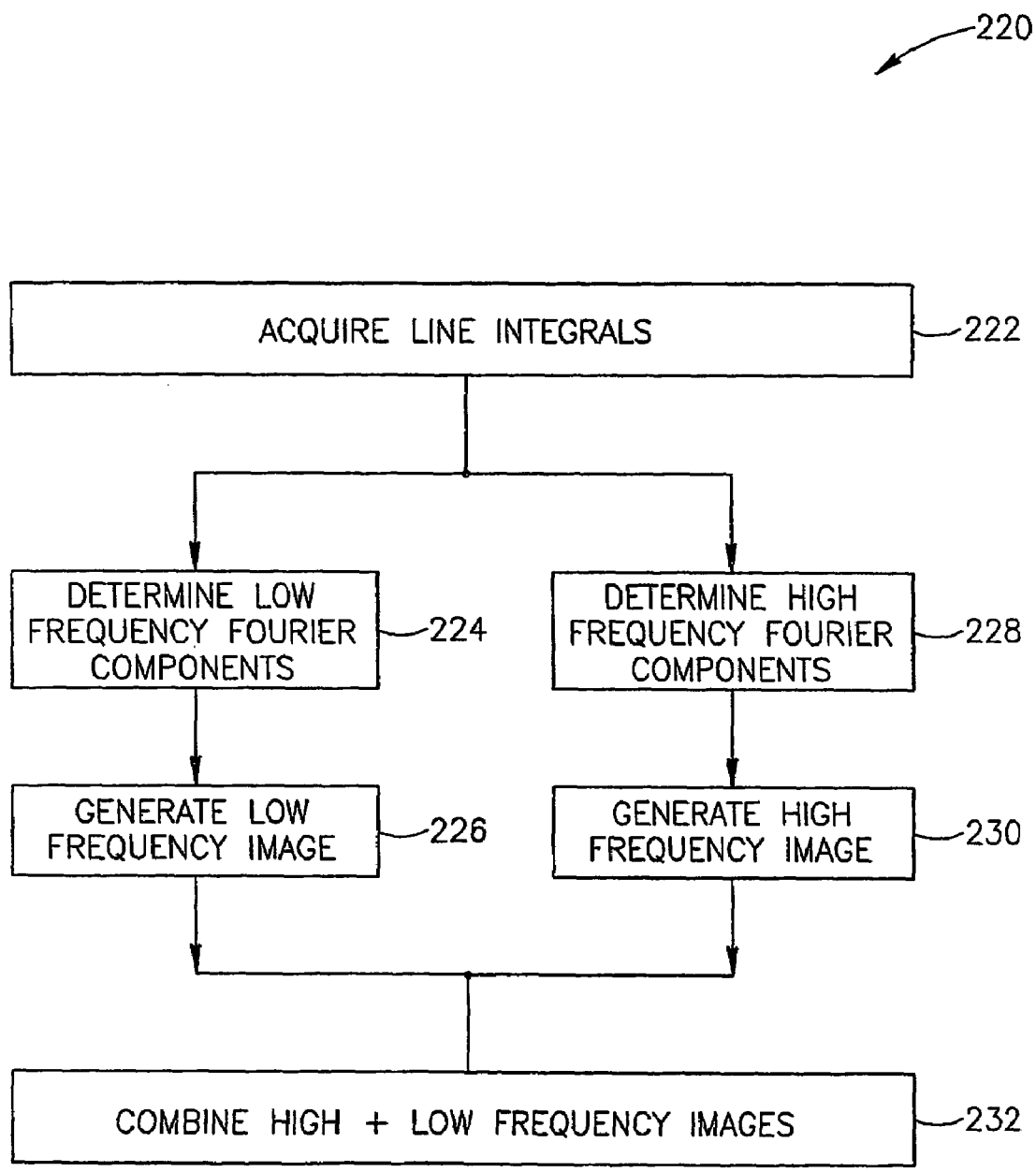
FIG. 9 shows a flow chart of a method of generating an image from data acquired by a CT scanner, in accordance with an embodiment of the present invention.

FIG. 9 shows a flow chart 220 of a method of generating a CT image of a region from line integral data of the region, in accordance with an embodiment of the present invention.

In a block 222 line integral data for the region is acquired. In a block 224 low spatial frequency components of a Fourier transform of the image are determined from the data and in a following block 226 the low frequency components are filtered and back projected to generate a low frequency image of the region. Optionally, filtering comprises filtering the low frequency data with a low frequency filter $f_L(\omega)$.

In a block 228 high spatial frequency components of the Fourier transform of the image are determined from the data and in a following block 230 the high frequency components are filtered and back projected to generate a high frequency image of the region. Optionally, filtering comprises filtering the high frequency data with a high frequency filter $f_H(\omega)$.

In a block 232 the low frequency and high frequency images are combined to provide an image of the region. Optionally, combining the low and high frequency images comprises weighting the images.

It is noted that whereas in the above discussion "offset data" is generated by offset rotating an X-ray beam, offset data can be generated using methods known in the art by using multiple X-ray sources. By way of example, U.S. Pat. No. 4,637,040, the disclosure of which is incorporated herein by reference, describes acquiring CT attenuation data using "at least two distinct point sources for emitting radiation". Methods in accordance with embodiments of the present invention for generating images from offset rotated data are applicable as well to processing multiple X-ray source data.

In the description and claims of the present application, each of the verbs, "comprise". "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

The invention claimed is:

1. A CT scanner for providing an image of a region comprising:
   at least one X-ray cone beam for illuminating the region with X-rays;
   a plurality of rows of X-ray detectors that generate signals responsive to line attenuation of X-rays from the at least one X-ray source that pass through the region;
   a controller that controls the at least one X-ray cone beam to acquire line attenuation data for the region for different view angles of the region; and
   a processor that receives the signals and:
   a) determines low spatial frequency components of the image from the data;
   b) generates a first spatial image of the region from the low frequency components;
   c) determines high spatial frequency components of the image from the data;
   d) generates a second spatial image of the region from the high frequency components; and
   e) combines the first and second images to generate the CT image.

2. A CT scanner according to claim 1 wherein the at least one X-ray cone beam is offset rotated.

3. A CT scanner according to claim 1 wherein the at least one X-ray cone beam comprises a plurality of X-ray cone beams.

4. A CT scanner according to claim 1 wherein the controller controls the at least one cone beam to acquire line attenuation data of the region for a span of view angles of about 360°.

5. A CT scanner according to claim 4 wherein the processor processes the line attenuation data to generate parallel views for the span of view angles.

6. A CT scanner according to claim 5 wherein the low frequency spatial components are band limited by a Nyquist frequency $\omega_N$ determined by a number of line integrals in a parallel view.

7. A CT scanner according to claim 6 wherein the low frequency spatial components are Fourier components.

8. A CT scanner according to claim 5 wherein the high frequency spatial components are band limited by a Nyquist frequency $2\omega_N$ determined by twice a number of line integrals in a parallel view.

9. A CT scanner according to claim 8 wherein the processor interleaves parallel views having an angular separation of 180° and Fourier transforms the interleaved parallel views to determine the high frequency Fourier components.

10. A CT scanner according to claim 8 wherein the processor interleaves parallel views with a number of null values equal to a number of line integrals in a parallel view and Fourier transforms the interleaved parallel views to determine the high frequency Fourier components.

11. A CT scanner according to claim 10 wherein to generate the second image the processor generates a first partial high frequency image from interleaved parallel views in a portion of the view angle span from 0° to about 180° and a second partial high frequency image from a portion of the view angle span from about 180° to about 360° and combines the first and second partial images.

12. A CT scanner according to claim 8 wherein the processor filters the high frequency data with a high band pass filter $f_H(\omega)$.

13. A CT scanner according to claim 12 wherein the high frequency filter $f_H(\omega)$ is equal substantially to zero for values of $\omega$ substantially less than $\omega_N$ and values of $\omega$ greater than $2\omega_N$.

14. A CT scanner according to claim 12 wherein $f_H(\omega)$ is substantially equal to one for values of $\omega$ in a neighborhood of $\omega_N$.

15. A CT scanner according to claim 12 wherein $f_H(\omega)$ decreases adiabatically to zero at a value $\omega$ in a neighborhood of $2\omega_N$.

16. A CT scanner according to claim 6 wherein the processor filters the low frequency components with a low frequency band pass filter $f_L(\omega)$.

17. A CT scanner according to claim 12 wherein the processor filters the low frequency components with a low frequency band pass filter $f_L(\omega)$.

18. A CT scanner according to claim 17 wherein the functions $f_H(\omega)$ and $f_L(\omega)$ are related by an expression $f(\omega)=f_H(\omega)+f_L(\omega)$ where $f(\omega)$ is equal substantially to one for values of $\omega$ substantially less than $\omega_N$ and equal to substantially zero for $\omega$ greater than $2\omega_N$.

19. A CT scanner according to claim 18 wherein $f(\omega)$ is equal substantially to one for values of $\omega$ in a neighborhood of $\omega_N$.

20. A CT scanner according to claim 18 wherein $f(\omega)$ decreases adiabatically to zero at a value of $\omega$ less than and in a neighborhood of $2\omega_N$.

21. A CT scanner according to claim 16 wherein low frequency filter $f_L(\omega)$ has non-zero values for $\omega$ less than $\omega_N$ and is equal to substantially zero for values of $\omega$ greater than $\omega_N$.

22. A CT scanner according to claim 16 wherein $f_L(\omega)$ is equal to substantially one for values of $\omega$ substantially less than $\omega_N$.

23. A CT scanner according to claim 16 wherein $f_L(\omega)$ adiabatically, decreases to zero at a value for $\omega$ in a neighborhood of $\omega_N$.

24. A method of generating a CT image from line attenuation data of a region comprising:
   determining low spatial frequency components of the image from the data;
   generating a first spatial image of the region from the low frequency components;
   determining high spatial frequency components of the image from the data;
   generating a second spatial image of the region from the high frequency components; and
   combining the first and second images to generate the CT image.

25. A method according to claim 24 wherein the line attenuation data comprises data acquired using an offset rotated X-ray cone beam.

26. A method according to claim 24 wherein the line attenuation data comprises data acquired using X-ray cone beams provided by a plurality of X-ray sources.

27. A method according to claim 24 wherein the line attenuation data comprises data from cone beam views of the region in a span of view angles of about 360°.

28. A method according to claim 27 wherein processing the line attenuation data comprises generating parallel views for the span of view angles.

29. A method according to claim 28 wherein determining low frequency spatial components comprises determining frequency components that are band limited by a Nyquist frequency $\omega_N$ determined by a number of line integrals in a parallel view.

30. A method according to claim 29 wherein determining the low frequency spatial components comprises Fourier transforming each parallel view to determine low frequency Fourier components.

31. A method according to claim 28 wherein determining high frequency spatial components comprises determining frequency components that are band limited by a Nyquist frequency $2\omega_N$ determined by twice a number of line integrals in a parallel view.

32. A method according to claim 31 wherein determining the high frequency Fourier components comprises generating interleaved parallel views by interleaving data from parallel views having an angular separation of 180° and Fourier transforming the interleaved parallel views to determine high frequency Fourier components.

33. A method according to claim 31 wherein determining the high frequency Fourier components comprises generating interleaved parallel views by interleaving data from each parallel view with a number of null values equal to a number of line integrals in a parallel view and Fourier transforming the interleaved parallel views.

34. A method according to claim 33 wherein determining the second image comprises generating a first partial high frequency image from interleaved parallel views in a portion of the view angle span from 0° to about 180° and a second partial high frequency image from a portion of the view angle span from about 180° to about 360° and combining the first and second partial images.

35. A method according to claim 31 and comprising filtering the high frequency data with a high band pass filter $f_H(\omega)$.

36. A method according to claim 35 wherein high frequency filter $f_H(\omega)$ is equal substantially to zero for values of $\omega$ substantially less than $\omega_N$ and values of $\omega$ greater than $2\omega_N$.

37. A method according to claim 35 wherein $f_H(\omega)$ is substantially equal to one for values of $\omega$ in a neighborhood of $\omega_N$.

38. A method according to claim 35 wherein $f_H(\omega)$ decreases adiabatically to zero at a value $\omega$ in a neighborhood of $2\omega_N$.

39. A method according to claim 29 and filtering the low frequency components with a low frequency band pass filter $f_L(\omega)$.

40. A method according to claim 35 and filtering the low frequency components with a low frequency band pass filter $f_L(\omega)$.

41. A method according to claim 40 wherein the functions $f_H(\omega)$ and $f_L(\omega)$ are related by an expression $f(\omega)=f_H(\omega)+f_L(\omega)$ where $f(\omega)$ is equal substantially to one for values of $\omega$ substantially less than $\omega_N$ and equal to substantially zero for $\omega$ greater than $2\omega_N$.

42. A method according to claim 41 wherein $f(\omega)$ is equal substantially to one for values of $\omega$ in a neighborhood of $\omega_N$.

43. A method according to claim 41 wherein $f(\omega)$ decreases adiabatically to zero at a value of $\omega$ less than and in a neighborhood of $2\omega_N$.

44. A method according to claim 39 wherein low frequency filter $f_L(\omega)$ has non-zero values for $\omega$ less than $\omega_N$ and is equal to substantially zero for values of $\omega$ greater than $\omega_N$.

45. A method according to claim 39 wherein $f_L(\omega)$ is equal to substantially one for values of $\omega$ substantially less than $\omega_N$.

46. A method according to claim 39 wherein $f_L(\omega)$ adiabatically, decreases to zero at a value for $\omega$ in a neighborhood of $\omega_N$.

47. A method of generating a CT image of a region from cone beam data comprising:
   acquiring line attenuation data for first and second parallel views of the region at view angles separated by an angular difference of 180°;
   interleaving data from each parallel view with null values;
   generating in accordance with a 3D back projection algorithm first and second images of the region using data in the first and second interleaved views respectively; and
   combining the first and second images to generate the CT image of the region.

* * * * *